US007985180B2

(12) United States Patent
Brown

(10) Patent No.: US 7,985,180 B2
(45) Date of Patent: Jul. 26, 2011

(54) EYELID RETRACTOR

(76) Inventor: Reay H Brown, Atlanta, GA (US)

( * ) Notice: Subject to any disclaimer, the term of this patent is extended or adjusted under 35 U.S.C. 154(b) by 916 days.

(21) Appl. No.: 11/937,021

(22) Filed: Nov. 8, 2007

(65) Prior Publication Data

US 2008/0108879 A1 May 8, 2008

Related U.S. Application Data

(60) Provisional application No. 60/864,870, filed on Nov. 8, 2006.

(51) Int. Cl.
A61B 1/32 (2006.01)
(52) U.S. Cl. ........................................ 600/236; 600/235
(58) Field of Classification Search .......... 600/218–236; 604/294–302; 606/107, 4–6
See application file for complete search history.

(56) References Cited

U.S. PATENT DOCUMENTS

| 2,702,540 | A | * | 2/1955 | Debeh | 600/218 |
| 4,321,916 | A | | 3/1982 | McKee | |
| 4,412,532 | A | | 11/1983 | Anthony | |
| 4,428,746 | A | * | 1/1984 | Mendez | 604/8 |
| 5,070,860 | A | | 12/1991 | Grounauer | |
| 5,341,798 | A | * | 8/1994 | Grounauer | 600/236 |
| 5,433,190 | A | | 7/1995 | Sunalp | |
| 5,441,040 | A | * | 8/1995 | Williams, Jr. | 600/236 |
| 5,618,261 | A | | 4/1997 | Nevyas | |
| 6,068,643 | A | * | 5/2000 | Milverton | 606/191 |
| 6,267,752 | B1 | | 7/2001 | Svetliza | |
| 6,283,913 | B1 | * | 9/2001 | Seibel | 600/236 |
| 6,440,065 | B1 | | 8/2002 | Hered | |
| 6,544,169 | B2 | | 4/2003 | Putrino et al. | |
| 7,175,594 | B2 | * | 2/2007 | Foulkes | 600/236 |
| 2007/0270657 | A1 | * | 11/2007 | Stephenson et al. | 600/236 |

FOREIGN PATENT DOCUMENTS

| EP | 1029508 | 8/2000 |
| WO | 89/05131 | 6/1989 |
| WO | 95/20917 | 8/1995 |

OTHER PUBLICATIONS

Lieberman, M.D., David M., An Improved Speculum, Ophthalmic Surgery, Aug. 1980, p. 528, vol. 11, No. 8, USA.

* cited by examiner

Primary Examiner — Eduardo C Robert
Assistant Examiner — Jan Christopher Merene
(74) Attorney, Agent, or Firm — Sutherland Asbill & Brennan LLP

(57) ABSTRACT

A device to retract the eyelids for ophthalmic surgery or other procedures by contacting the inner surfaces of the upper and lower eyelids with a frame that applies point contact to the tissue in at least three non-linear locations across the upper lid. The upper and lower retractor frames are connected to distensible arms with a means to allow the frames to move from a first insertion position to a second retracted position for use. The eyelid retractor may further be provided with one or more suture retaining cleats to removably secure stay sutures placed for added surgical exposure without the need to tie or otherwise manipulate such sutures.

7 Claims, 5 Drawing Sheets

EYELID RETRACTOR

CROSS REFERENCES TO RELATED APPLICATIONS

This application claims priority to Provisional Patent Application No. 60/864,870 filed on Nov. 8, 2006, and incorporates by reference its entirety herein.

FIELD OF THE INVENTION

The present invention relates to a device for use in retracting an eyelid to expose an eyeball. Particularly, the present invention relates to a device that exposes an eyeball to allow greater access to the exposed surface of the eyeball during eye surgery, eye examination, or other procedures involving instrumentation or manipulation of the eye.

BACKGROUND

Many eyelid retracting devices are described in the prior art. In U.S. Pat. No. 5,433,190 to Sunalp, an eyelid speculum device is disclosed. It is used to hold a person's eyelids open for ocular surgery, treatment, examination, or other reason. It may be inserted between the upper and lower eyelids of a person's eye.

In U.S. Pat. No. 5,618,261 to Nevyas, an eye proposing speculum that applies pressure to urge the eyeball outwardly is disclosed. The speculum includes a pair of blades and a pair of pressors. Each blade is shaped to engage a patient between one of the eyelids and the eyeball.

In U.S. Pat. No. 4,321,916 to McKee, an eyelid retractor comprises a loop having a smooth surface with eyelid restraining blades positioned on opposite sides thereof. The retractor is sufficiently malleable to be in elastically deformed such that the blades are in a desired eyelid retracting configuration and the retractor loop is also bent to conform to the face of the patient such that the retractor is supported by the face.

U.S. Pat. No. 6,544,169 to Putrino discloses an eye retraction device that comprises a pair of arms connected at a joint. The arms are in a wishbone form with a size and configuration that accommodate the anatomy of the eye. The arms can be embodied in several preferred ways so that the size and configuration of the wishbone can be changed dynamically, adjusted resiliently, or fixed manually.

In U.S. Pat. No. 6,267,752 to Svetliza, the eyelid speculum is provided as a truncated cone-shaped main body with lid retractors tending out of it in the form of a ring, forming an angle appropriate to the curvature of the eye.

The prior art devices retract the eyelid, but provide uneven exposure, particularly to the superior conjunctival margin in an anesthetized patient. The spreading action of such existing devices provides relatively wide exposure at the lateral and medial margins, but lesser exposure superiorly or inferiorly. This is particularly problematic in an anesthetized eye, where the Bell's reflex action tends to move the eye into a relative upward gaze position, further compromising the surgical exposure from the eyelid retractor. Some surgical procedures, notably for glaucoma, require an incision in the superior margin of the sclera. There exists a need, therefore, for an eyelid retracting device that can deliver better surgical exposure to the superior conjunctival margin of the sclera.

Moreover, existing prior art eyelid retractors offer either two-point contact with the medial and lateral aspects of the upper and lower eyelids (which fails to adequately retract the middle portions of the lids, decreasing exposure inferiorly and superiorly), or a bladed design which applies potentially injurious pressure to the whole of the delicate palpebral conjunctival surfaces. The need exists, therefore, for an eyelid retracting device that can deliver better surgical exposure to the superior and inferior conjunctival margins of the sclera, with reduced pressure on the palpebral conjunctival surfaces. The need exists also for an eyelid retracting device that prevents eyelashes from everting during surgery to minimize the risk of infection associated therewith.

SUMMARY OF THE INVENTION

The present invention provides an eyelid retractor for displacing eyelids away from a position in which they would cover an eye upon which ocular surgery or a similar procedure is being performed. In a preferred embodiment, the retractor comprises a body with a continuous loop having no sharp or pointed edges upon which suture thread may snag or break. Preferably, eyelid engaging portions, or zones, on the retractor are integral with the structure of the loop. The retractor device retracts at least the upper eyelid, and optionally the lower eyelid, with an open frame configuration having at least three distinct non-linear eyelid contact zones such that the medial aspect of the eyelid is opened more widely than the distal or proximal corresponding aspects with minimal pressure on the eyelid and eye.

The eyelid retractor according to the present invention preferably incorporates cleats or other fasteners at selected locations along the body of the retractor, configured to receive and hold sutures placed by the surgeon during the surgery or other procedure. Such cleats or fasteners may be simple posts, about which sutures may be secured. In a preferred embodiment, such cleats or fasteners may be provided to receive and hold sutures placed therein, without the need for tying or further manipulation of such sutures, thereby substantially reducing operating time.

The eyelid retractor according to the present invention may be used in conjunction with a surgical microscope, slit lamp, indirect opthalmoscope, or other instruments used in eye surgery or eye care procedures. Once in position on the patient, the retractor of the present invention need not be removed until the operation is completed.

The eyelid retractor according to the present invention preferably may be provided as a disposable, single-use item. Alternately, embodiments of the eyelid retractor according to the present invention may be provided for repeated usage following cleaning and sterilization between uses.

BRIEF DESCRIPTION OF THE DRAWINGS

The objects and advantages of the present invention will be better understood and more readily apparent when considered in conjunction with the following detailed description and accompanying drawings which illustrate, by way of example, preferred embodiments of the invention and in which.

DETAILED DESCRIPTION OF THE PREFERRED EMBODIMENT

Figure 1:
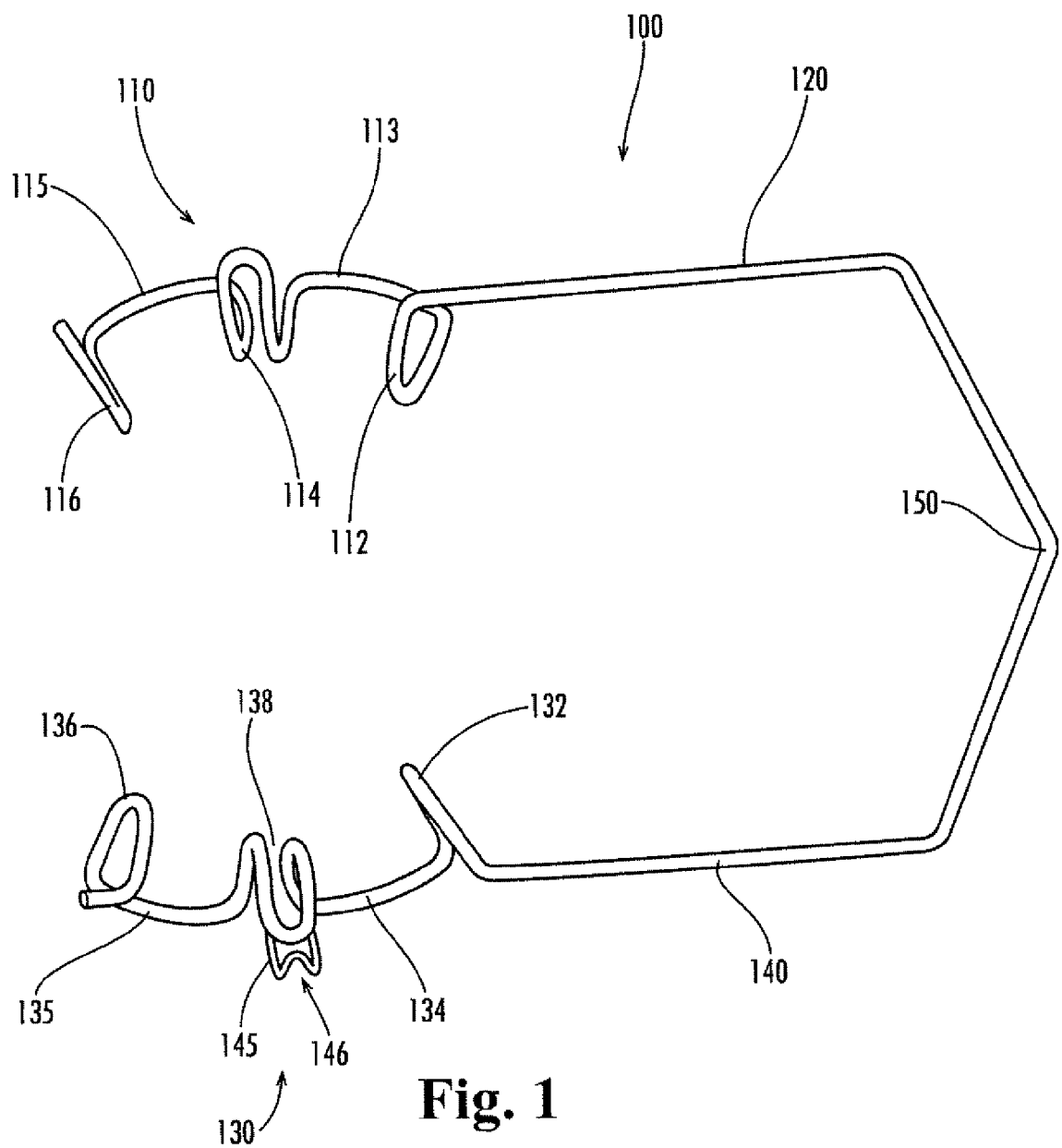
FIG. 1 provides an overhead view of an exemplary eyelid retractor according to the present invention.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention provides a retractor for use in retracting the eyelids. The device employs the friction or adhesion between contacting zones of the device and the outer surface of the eyelid and retracts the eyelids to expose the eyeball to assist an eye care clinician, such as an optometrist, an ophthalmologist, or an ophthalmic or optometric technician, to gain greater access to the exposed surface of the eyeball during an eye care procedure, such as a routine examination, a diagnostic procedure, a therapeutic procedure, or a surgery.

For certain types of ophthalmic surgical procedures, such as in glaucoma-related surgery, an incision must be made far superior to the surgical limbus of the eye, in the sclera and well above the iris, and it is for these types of situations that an eyelid retractor is most useful. The eyelid retractor according to the present invention operates by applying forces to displace the inner, conjunctival surfaces of the upper eyelids superiorly and lower eyelids inferiorly, without causing excessive pressure across the entire eye and eyelids. Furthermore, the eyelid retractor according to the present invention operates by preventing eyelid eversion during surgery which can otherwise lead to infection.

The present invention provides an eyelid retracting device for retracting upper and lower eyelids to expose an eyeball, wherein the device generally has an upper eyelid retracting frame and attached upper distensible arm, and an opposing lower eyelid retracting frame and attached lower distensible arm, and a union connecting the upper and lower arm elements.

In general, the device and parts thereof may be referred to herein as having proximal, medial and distal aspects from the perspective of the operator using the retractor device. In certain embodiments, the upper eyelid retracting frame has at least three upper eyelid retracting zones, corresponding to the proximal aspect, the medial aspect and the distal aspect, connected in non-linear alignment by support bridges. The retracting zones make contact the outer edges of the eyelid, and are non-contiguous, thus, allowing eyelid tissue to be exposed therebetween to minimize the application of pressure across the eyelid and eye generally during retraction. In example embodiments, these non-contiguous zones of contact are achieved with the use of a metallic wire frame structure, described in more detail below.

The at least three, or more, upper retracting zones are in non-linear alignment, wherein the medial retracting zone is upwardly displaced so as to form an angle of less than 180 degrees towards the eye between the vectors created from proximal upper eyelid retracting zones and the distal upper eyelid retracting zone to raise the medial portion of the upper eyelid open more than the proximal and the distal portions of the upper eyelid. Preferably, the angle created by the vectors connecting the most medial retracting zone to each of the proximal and distal retracting zones is about between 90 and 180 degrees, and more preferably between about 120 and 170 degrees. In various other embodiments, the upper retracting frame can have four, five, six or more retracting zones, such that the retracting zone of the most medial zone(s) raise the eyelid more across the middle than in the lateral aspects.

The opposing lower eyelid retracting frame also has a proximal aspect, a medial aspect and a distal aspect and comprises at least two, or more, lower eyelid retracting zones corresponding to the lateral aspects of the lower eyelid. In certain embodiments, as more fully explained below, the lower eyelid retracting frame may include three or more lower eyelid retracting zones, similar to that previously described with respect to the upper retracting zones. Again, the multiple lower eyelid retraction zones make contact with the eyelid in a non-contiguous manner across the edges of the eyelid, and are connected to one another by a support bridge. In certain other embodiments, the lower eyelid retracting frame further comprises a fourth, fifth, sixth, or more medial eyelid retracting zones, connected to the distal and proximal lower eyelid retracting zones by separate bridges, wherein the medial retracting zones are downwardly displaced so as to form an angle towards the eye between the proximal lower eyelid retracting zone and the distal lower eyelid retracting zone to move the medial portion of the lower eyelid open more than the proximal and the distal portions of the lower eyelid. Preferably, the angle created by the vectors connecting the most medial retracting zone to each of the proximal and distal retracting zones is between about 90 and 180 degrees, and more preferably between about 120 and 160 degrees.

The invention provides that the distance between retracting zones, on either the upper or lower arms, can be equidistant or variable. In particular, the invention provides preferred embodiments wherein the distance from the distal retracting zone to the medial retracting zone is greater than the distance from the medial retracting zone to the proximal retracting zone.

In certain embodiments, the bridges of the upper eyelid retracting frame are adapted to lie under the upper eyelid in the retracted position. In certain embodiments, the bridges of the upper eyelid retracting frame are adapted to lie outside the upper eyelid in the retracted position. In other embodiments, the bridges of the lower eyelid retracting frame are adapted to lie under the lower eyelid in the retracted position. In still other embodiments, the bridges of the lower eyelid retracting frame are adapted to lie outside the lower eyelid in the retracted position.

The eyelid retracting device further comprises an upper distensible arm attached to the proximal aspect of the upper eyelid retractor frame, capable of displacement from a first insertion position to a second retracted position. Furthermore, the device comprises a lower distensible arm attached to the proximal aspect of the lower eyelid retractor frame capable of displacement from a first insertion position to a second retracted position.

The upper distensible arm and the lower distensible arm are connected at a union that permits relative displacement of the upper and lower distensible arms. In certain embodiments, the upper and/or lower frames are constructed of a contiguous piece of wire or other similar shape-memory material. In other embodiments, the entire device is constructed of a contiguous piece of wire. In certain embodiments, the union provides a biasing force to maintain the upper and lower eyelids in a retracted position, either as a function of its shape-memory properties or through a variety of mechanical biasing or locking means known in the art of surgical instruments.

The invention also provides that one or more suture cleats can be affixed to the upper frame, lower frame, upper distensible arm or lower distensible arm. The cleats may have a dimple or similar grooved surface feature to assist in the temporary securing of a stay suture, such as placed through the sclera, to keep the eye from rotating during surgery.

Reference is now made to certain specific non-limiting embodiments as shown in the Figures. FIG. 1 shows an eyelid retracting device 100 comprising an upper eyelid retracting frame 110 and an attached upper distensible arm 120, and an opposing lower eyelid retracting frame 130 and attached lower distensible arm 140, and a union 150 connecting these upper and lower elements.

The upper eyelid retracting frame 110 has at least three upper eyelid retracting zones, corresponding to the proximal aspect zone 112, the medial aspect zone 114 and the distal aspect zone 116, connected in non-linear alignment by support bridges 113, 115. The retracting zones 112, 114, 116 make contact with the outer edge of the upper eyelid allowing the superior portion of the eye to be exposed.

As can be seen in FIG. 1, the three upper retracting zones 112, 114, 116 may be arranged in non-linear alignment, wherein the medial retracting zone 114 is upwardly displaced so as to form an angle of less than 180 degrees towards the eye defined by the vectors connecting the medial retracting zone 114 to each of the proximal retracting zone 112 and the distal retracting zone 116. This angle raises the medial portion of the upper eyelid open more than the proximal and the distal portions of the upper eyelid. This angle is shown to be about 120 degrees. In other embodiments, the arrangement of the upper retracting zones 112, 114, 116 may be substantially straight, displacing the upper eyelid in generally the same plane.

In this example embodiment, the opposing lower eyelid retracting frame 130 comprises at least three lower eyelid retracting zones 132, 138, 136 corresponding to the point of contact with the edge of the lower eyelid. The three retraction zones 132, 138, 136 of the lower frame 130 make contact in a non-contiguous manner across the edges of the lower eyelid, and are connected to one another by at least two support bridges 134, 135. An embodiment having more than three lower eyelid retracting zones would have a support bridge between each retracting zone.

The three lower retracting zones 132, 138, 136 may be arranged in non-linear alignment, wherein the medial retracting zone 138 is downwardly displaced so as to form an angle of less than 180 degrees towards the eye defined by the vectors connecting the medial retracting zone 138 to each of the proximal retracting zone 132 and the distal retracting zone 136. This angle displaces the medial portion of the lower eyelid open more than the proximal and the distal portions of the lower eyelid. This angle here is shown to be about 120 degrees. However, it is appreciated that in other example embodiments, the lower retracting zones 132, 138, 136 may be a substantially straight, as is illustrated and described more fully below in reference to FIG. 5, displacing the lower eyelid in generally the same plane.

In the example embodiment shown in FIG. 1, the support bridges 113, 115 of the upper eyelid retracting frame 110 are adapted to lie under the upper eyelid in the retracted position. In this embodiment, the support bridges 134, 135 of the lower eyelid retracting frame 130 are also adapted to lie under the lower eyelid in the retracted position.

In one example embodiment shown in FIG. 1, the lower retracting frame 130 may optionally be equipped with a suture cleat 145 attached to the medial retraction zone 138 shown with a dimple 146 for frictionally maintaining a suture therein. The optional suture cleat 145 and suture to be maintained thereon allow for temporarily anchoring the eye in a downward position, at the discretion of the surgeon. It is appreciated that a suture cleat as is shown as the suture cleat 145 in FIG. 1 may be optionally included on any of the upper retracting zones 112, 114, 116 or on any of the lower retracting zones 132, 138, 136, or any combination thereof. Furthermore, multiple suture cleats may be included on a single retracting zone of the device.

The eyelid retracting device 100 shown in FIG. 1 further comprises an upper distensible arm 120 attached to the proximal aspect of the upper eyelid retractor frame 110, capable of displacement from a first insertion position to a second retracted position. Furthermore, the device 100 comprises a lower distensible arm 140 attached to the proximal aspect of the lower eyelid retractor frame 130 capable of displacement from a first insertion position to a second retracted position. The upper distensible arm 120 and the lower distensible arm 140 are connected at a union 150 that permits relative displacement of the upper and lower distensible arms 120, 140. In the embodiment shown, the upper and/or lower frames 110, 130 are constructed of a contiguous piece of wire as a shape-memory material, and indeed, the entire device 100 is constructed of a contiguous piece of wire. However, it is appreciated that the upper frame 110 and the lower frame 130 may be separately constructed and the two members may be connected at the union 150, as would be known in the art.

Figure 2:
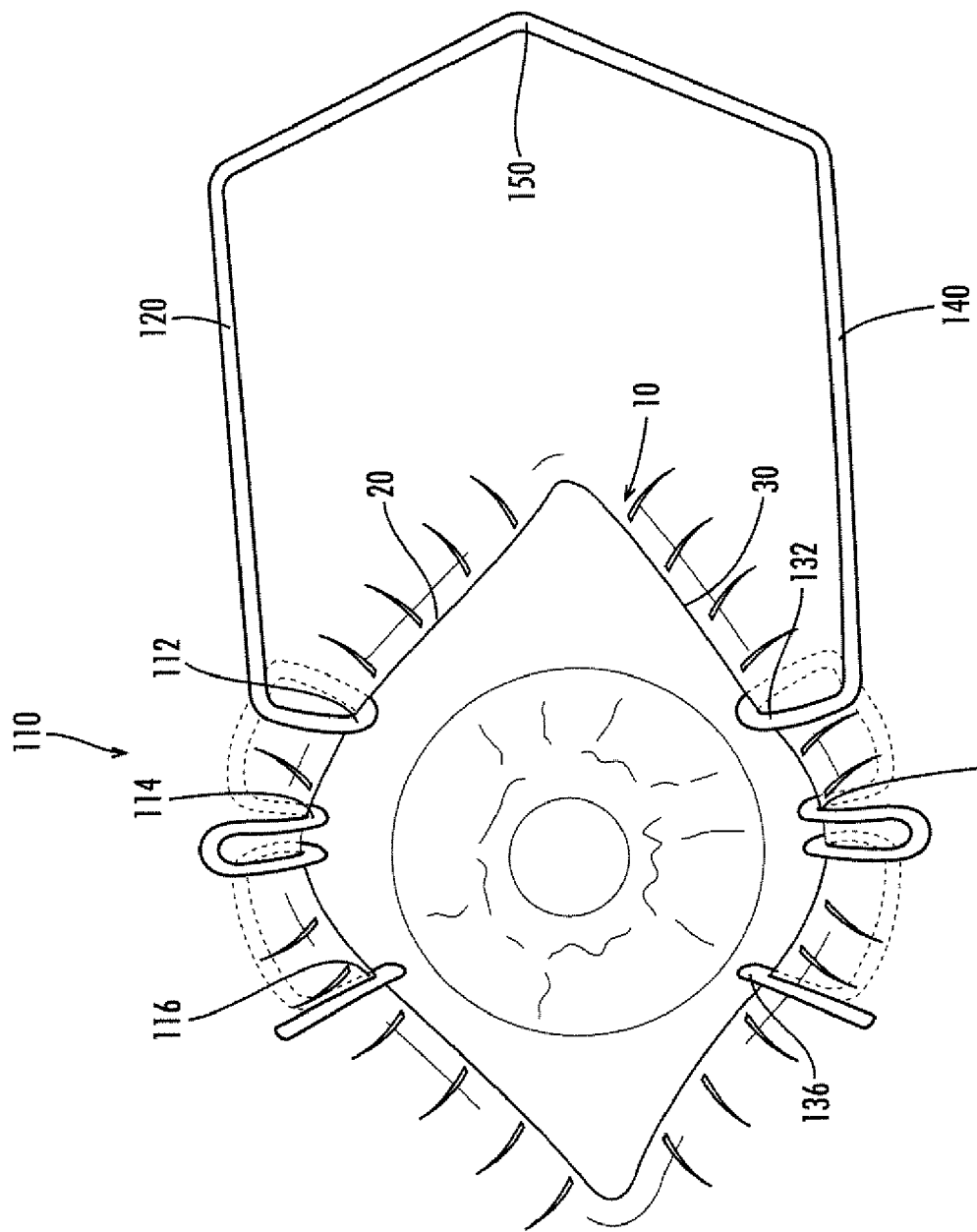
FIG. 2 provides a perspective view of an exemplary eyelid retractor according to the present invention in use in the left eye of a patient.

FIG. 2 shows the use of an exemplary eyelid retractor 100 according to the present invention operatively in use in a left eye 10. Extruding from the upper retracted eyelid 20 can be seen the proximal retracting zone 112, the medial retracting zone 114, and the distal retracting zone 116 of the upper retracting frame 110, which is attached to the upper distensible arm 120. Extruding from the lower retracted eyelid 30 can be seen the proximal retracting zone 132, the medial retracting zone 138, and the distal retracting zone 136 of the lower retracting frame 130, which is attached to the lower distensible arm 140. The union 150 connecting the upper and lower distensible arms 120, 140 is also shown. In an alternate embodiment where the lower retracting frame 130 only includes a proximal retracting zone 132 and a distal retracting zone 136, such as the example embodiment illustrated in FIG. 5, the lower eyelid would be displaced at the two zone points in a substantially straight plane.

The particular embodiments shown in FIGS. 1 and 2 that include at least three lower eyelid retracting zones 132, 138, 136, have an advantage of further minimizing the risk of lower eyelid eversion during surgery. Additionally, embodiments such as this having an equal number of retraction zones on the upper and lower frames advantageously permit the device to be used interchangeably on both left and right eyes.

Figure 3:
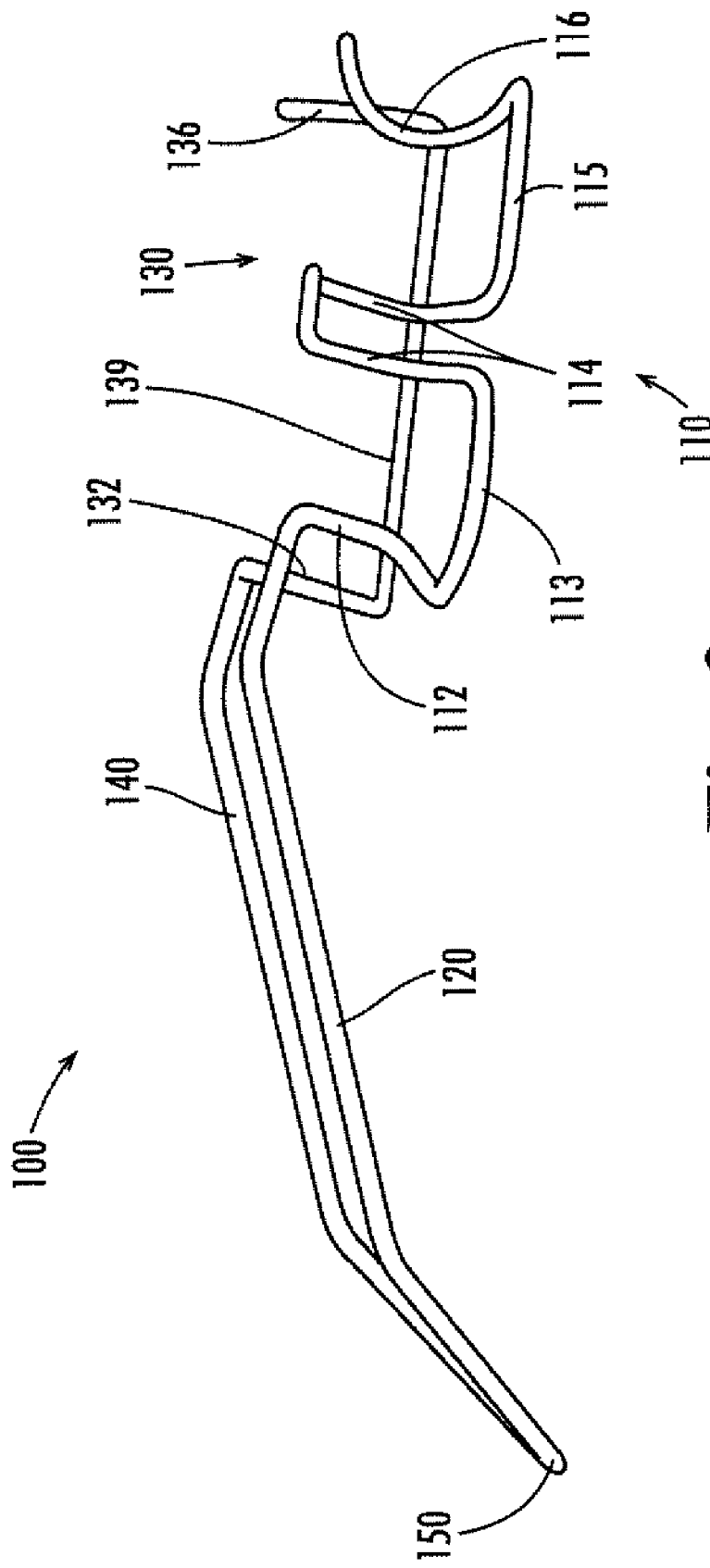
FIG. 3 provides a side view of an exemplary eyelid retractor according to the present invention.

FIG. 3 shows a side view of the present invention wherein the device 100 comprises an upper eyelid retracting frame 110 and an attached upper distensible arm 120, and an opposing lower eyelid retracting frame 130 and attached lower distensible arm 140, and a union 150 connecting these upper and lower elements.

The upper eyelid retracting frame 110 has three upper eyelid retracting zones, corresponding to the proximal aspect zone 112, the medial aspect zone 114 and the distal aspect zone 116, connected in non-linear alignment by support bridges 113, 115. The retracting zones 112, 114, 116 make contact with the outer edge of the upper eyelid.

As can be seen in the example embodiment illustrated in FIG. 3, the opposing lower eyelid retracting frame 130 comprises at least two lower eyelid retracting zones 132, 136 corresponding to the point of contact with the edge of the lower eyelid 30. The two retraction zones 132, 136 of the frame 130 make contact in a non-contiguous manner across the edges of the lower eyelid 30, and are connected to one another by a support bridge 139. In the embodiment shown in FIG. 1, the support bridges 113, 115 of the upper eyelid retracting frame 110 are adapted to lie under the upper eyelid in the retracted position. In this embodiment, the support bridge 139 of the lower eyelid retracting frame 130 is also adapted to lie under the lower eyelid in the retracted position. An alternate view of a similar embodiment having only two lower retracting zones is further illustrated and described with reference to FIG. 5.

The eyelid retracting device 100 shown in FIG. 3 further comprises an upper distensible arm 120 attached to the proximal aspect of the upper eyelid retractor frame 110, capable of displacement from a first insertion position to a second retracted position. Furthermore, the device 100 comprises a lower distensible arm 140 attached to the proximal aspect of the lower eyelid retractor frame 130 capable of displacement from a first insertion position to a second retracted position. The upper distensible arm 120 and the lower distensible arm 140 are connected at a union 150 that permits relative displacement of the upper and lower distensible arms 120, 140. In the embodiment shown, the upper and/or lower frames 110, 130 are constructed of a contiguous piece of wire as a shape-memory material, and indeed, the entire device 100 is constructed of a contiguous piece of wire. However, it is appreciated that the upper frame 110 and the lower frame 130 may be separately constructed and connected at the union 150.

Figure 4:
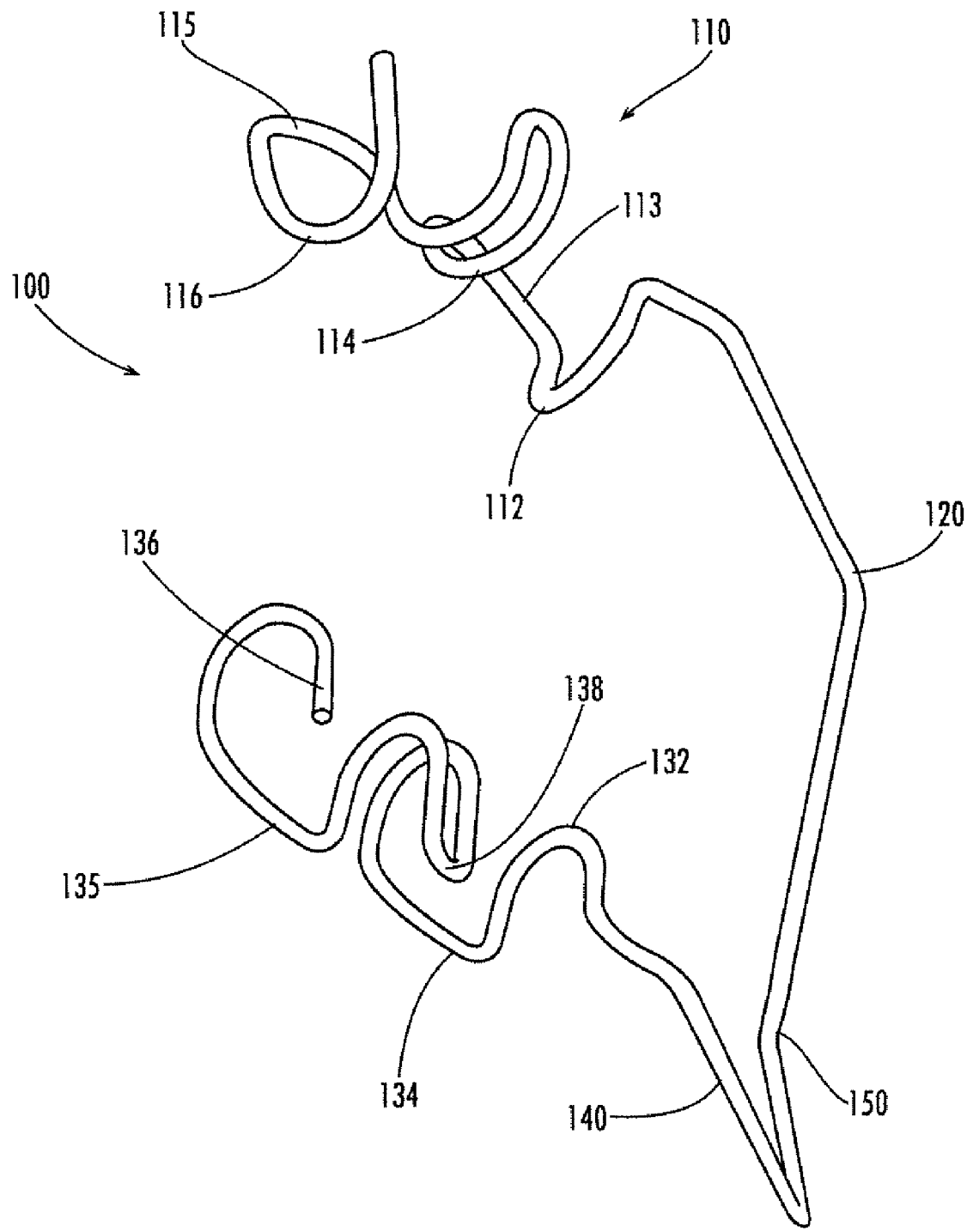
FIG. 4 provides a perspective view of an exemplary eyelid retractor according to the present invention.

FIG. 4 presents a perspective view of the present invention wherein the device 100 comprises an upper eyelid retracting frame 110 and an attached upper distensible arm 120, and an opposing lower eyelid retracting frame 130 and attached lower distensible arm 140, and a union 150 connecting these upper and lower elements. In this example embodiment, the upper eyelid retracting frame 110 has three upper eyelid retracting zones, corresponding to the proximal aspect zone 112, the medial aspect zone 114 and the distal aspect zone 116, connected in non-linear alignment by support bridges 113, 115. The retracting zones 112, 114, 116 make contact with the outer edge of the upper eyelid allowing the superior portion of the eye to be exposed.

As can be seen in FIG. 4, the three upper retracting zones 112, 114, 116 are in non-linear alignment, wherein the medial retracting zone 114 is upwardly displaced so as to form an angle of less than 180 degrees towards the eye defined by the vectors connecting the medial retracting zone 114 to each of the proximal retracting zone 112 and the distal retracting zone 116. This angle raises the medial portion of the upper eyelid open more than the proximal and the distal portions of the upper eyelid. This angle here is shown to be about 120 degrees.

The opposing lower eyelid retracting frame 130 of this example embodiment comprises three lower eyelid retracting zones 132, 138, 136 corresponding to the point of contact with the edge of the lower eyelid 30. The three lower eyelid retraction zones 132, 138, 136 of the frame 130 make contact in a non-contiguous manner across the edges of the lower eyelid, and are connected to one another by support bridges 134, 135.

Figure 5:
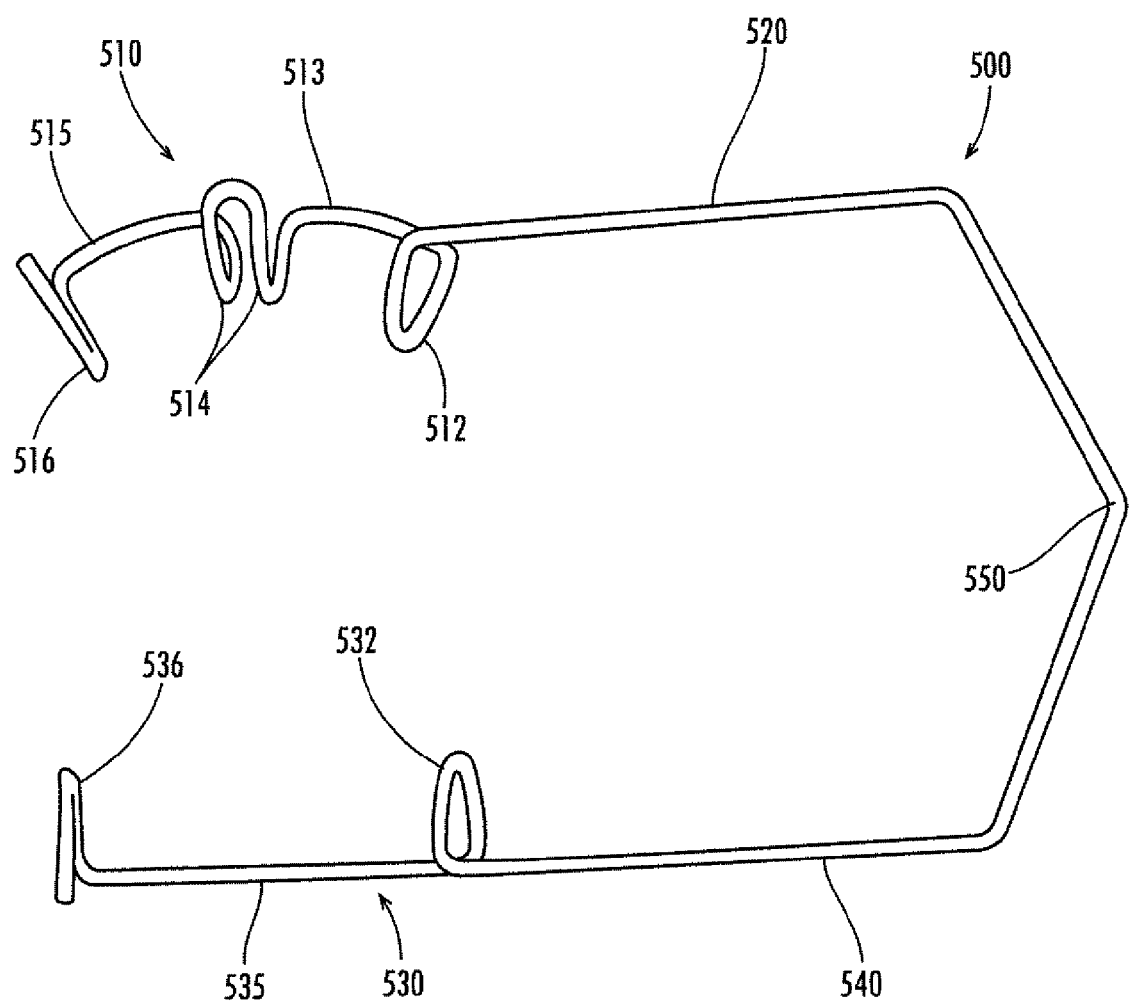
FIG. 5 provides a perspective view of an alternative preferred embodiment of eyelid retractor according to the present invention.

Referring now to FIG. 5, an alternative embodiment is shown wherein the lower eyelid retracting frame 530 comprises only two lower eyelid retracting zones 532, 536. Furthermore, this alternative embodiment illustrates at least the lower eyelid retracting frame 530 formed as a substantially straight member.

In particular, this example embodiment further provides a device 500 comprising an upper eyelid retracting frame 510 and an attached upper distensible arm 520, and an opposing lower eyelid retracting frame 530 and attached lower distensible arm 540, and a union 550 connecting these upper and lower elements. The upper eyelid retracting frame 510 has three upper eyelid retracting zones, corresponding to the proximal aspect zone 512, the medial aspect zone 514 and the distal aspect zone 516, connected in non-linear alignment by support bridges 513, 515. The retracting zones 512, 514, 516 make contact with the outer edge of the upper eyelid allowing the superior portion of the eye to be exposed. However, in alternate embodiments, the upper eyelid retracting frame 510 may include two retracting zones or may include more than three retracting zones.

As can be seen in FIG. 5, the lower eyelid retracting frame 530 has two lower eyelid retracting zones, corresponding to the proximal aspect zone 532 and the distal aspect zone 536, connected in a substantially straight alignment by a support bridges 530. The two lower retracting zones 532, 536 make contact with the outer edge of the lower eyelid allowing the inferior portion of the eye to be exposed.

It is noted that while the present invention has been described in use as an eyelid retractor, such a retractor could be equivalently utilized for other medical purposes, including retraction of other bodily orifices or tissues. The present invention contemplates methods of use of the devices described above, comprising retracting tissues of a patient in need thereof with any of said devices. Furthermore, the invention is not limited to any materials, coatings thereon or particular dimensions, as such may be readily adapted by one of skill in the art suitable for the desired mechanical and therapeutic properties and the particular size of a patient.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. An eyelid retracting device for retracting upper and lower eyelids to expose an eyeball, said device comprising:
   a. an upper eyelid retracting frame having a proximal aspect with a proximal upper eyelid retracting zone, a medial aspect with a medial upper eyelid retracting zone and a distal aspect with a distal upper eyelid retracting zone, wherein the proximal, medial and distal upper eyelid retracting zones are connected in non-linear alignment by separate support bridges, wherein the medial upper eyelid retracting zone is upwardly displaced so as to form an angle towards the eye between the proximal upper eyelid retracting zone and the distal upper eyelid retracting zone to raise the medial portion of the upper eyelid open more than the eyelid at the proximal and the distal upper eyelid retracting zones, wherein the support bridges of the upper eyelid retracting frame are adapted to lie under the upper eyelid in the retracted position, and wherein the upper frame is constructed of a piece of wire;
   b. an opposing lower eyelid retracting frame having a proximal aspect with a proximal lower eyelid retracting zone, a medial aspect with a medial lower eyelid retracting zone and a distal aspect with a distal lower eyelid retracting zone, wherein the proximal, medial and distal lower eyelid retracting zones are connected in non-linear alignment by separate a support bridges, wherein the medial lower eyelid retracting zone is downwardly displaced so as to form an angle towards the eye between the proximal lower eyelid retracting zone and the distal lower eyelid retracting zone to move the medial portion of the lower eyelid open more than the proximal and the distal portions of the lower eyelid, wherein the bridges of the lower eyelid retracting frame is adapted to lie under the lower eyelid in the retracted position, and wherein the lower frame is constructed of a piece of wire;

c. an upper distensible arm attached to the proximal aspect of the upper eyelid retractor frame capable of displacement from a first insertion position to a second retracted position;

d. a lower distensible arm attached to the proximal aspect of the lower eyelid retractor frame capable of displacement from a first insertion position to a second retracted position; and e. a union between the upper distensible arm and the lower distensible arm that permits relative displacement of the upper and lower distensible arms.

2. The device of claim 1, wherein the wire of the upper frame and the wire of the lower frame are the same piece of wire.

3. The device of claim 1, wherein the union provides a biasing force to maintain the upper and lower eyelids in a retracted position.

4. The device of claim 1, further comprising a stay suture cleat affixed to the lower eyelid retracting frame.

5. The device of claim 1, further comprising a stay suture cleat affixed to the upper eyelid retracting frame.

6. The device of claim 1, wherein the distance between the upper distal and medial eyelid retracting zones is greater than the distance between the upper proximal and medial eyelid retracting zones.

7. The device of claim 1, wherein the distance between the lower distal and medial eyelid retracting zones is greater than the distance between the lower proximal and medial eyelid retracting zones.

* * * * *